United States Patent

Takinishi et al.

[11] 4,310,002
[45] Jan. 12, 1982

[54] ELECTROPALATOGRAPH

[75] Inventors: Kiyotoshi Takinishi, Koganei; Shingi Iwasaki, Tachikawa, both of Japan

[73] Assignee: Rion Co., Ltd., Tokyo, Japan

[21] Appl. No.: 150,216

[22] Filed: May 15, 1980

[30] Foreign Application Priority Data

May 18, 1979 [JP] Japan .................. 54/61341

[51] Int. Cl.³ .................. A61B 5/10; G09B 19/04
[52] U.S. Cl. .................. 128/642; 128/777; 434/185
[58] Field of Search .................. 128/639–644, 128/787, 798, 903, 777; 434/185

[56] References Cited

U.S. PATENT DOCUMENTS

| 3,815,109 | 6/1974 | Carraway et al. | 128/903 X |
| 3,815,583 | 6/1974 | Scheidt | 128/903 X |
| 4,112,596 | 9/1978 | Fletcher et al. | 434/185 X |
| 4,175,338 | 11/1979 | Takinishi et al. | 434/185 X |

OTHER PUBLICATIONS

Fletcher, S. G. et al., *J. Speech & Hearing Res.*, vol. 18, No. 4, (Dec. 1975).

*Primary Examiner*—Kyle L. Howell
*Attorney, Agent, or Firm*—Leydig, Voit, Osann, Mayer & Holt

[57] ABSTRACT

An electropalatograph for speech training and the like, which electrically detects linguapalatal contact mode during phonations by means of many contact sensing electrodes provided on a surface with which trainee's tongue contacts of artificial palate device mounted to hard palate surface of the trainee, detected informations denoting the contact mode are transmitted as electromagnetic waves from a transmitter disposed within the trainee's mouth, and transmitted waves are received by a receiver disposed outside the trainee's body and displayed to be observed as dynamic patterns of actual linguapalatal contact mode.

5 Claims, 3 Drawing Figures

ELECTROPALATOGRAPH

This invention relates generally to electropalatographs for articulation study, speech training and the like and, more particularly, to improvements in the electropalatograph wherein an artificial palate having many sensing electrodes on the surface with which a trainee's tongue contacts when fitted to hard palate surface of the trainee and, during his phonations, such actual linguapalatal contact mode is electrically detected and, generally, the detected mode is observably displayed on a display device so that the trainee's articulation study and correct speech training can be accomplished while observing dynamic patterns of the actual contact mode.

Conventionally, in performing the articulation and speech training using the electropalatograph of the kind referred to, as seen in FIG. 1, an artificial palate device 101 provided with many sensing electrodes is fitted intimately to the hard palate surface of a trainee, many lead wires connected to the respective sensing electrodes are divided into two right and left bundles and these bundles are extended in the form of two cords 102 and 103 along outside the tooth rows of the trainee from the rear or innermost end edge of the artificial palate device 101, respectively pulled out of the mouth from both right and left ends of the mouth and connected directly or after being once hung on the ears to an electropalatograph display device 104. Generally, in the artificial palate device 101, in order to accurately obtain the linguapalatal contact pattern, 64 sensing electrodes distributed substantially all over the tongue contacting surface of the artificial palate are used and each of the lead wire cords 102 and 103 includes 32 insulation-coated lead wires and becomes comparatively thick. Therefore, the trainee must make the phonation or speech while having these two cords positioned at both ends of the mouth so that the conventional electropalatograph has had to involve such defects that the trainee must be trained while always having unpleasant or unnatural feeling due to such cords, some phonations being difficult to be correctly performed because of the cords, and saliva in the mouth flowing out along the cords so as to hinder the phonations and cause a sanitation problem. The present invention has been suggested in view of these defects of the conventional electropalatographs.

A primary object of the present invention is, therefore, to provide an electropalatograph which allows articulation and speech trainees to perform natural phonations or speeches without having any unnatural feeling during the use.

Another object of the present invention is to provide an electropalatograph which employs no element obstructing all kinds of phonations required for the articulation and speech training.

A related object of the present invention is to provide an electropalatograph which allows the trainees to perform natural phonations or speeches without using lead wire cords pulled out of the mouth through both end portions of the lips of the trainee and linguapalatal contact modes can be accurately detected.

Other objects and advantages of the present invention shall be made clear upon reading the following disclosure of the present invention detailed with reference to a preferred embodiment shown in accompanying drawings, in which.

While the present invention shall be detailed with reference to the illustrated embodiment, the intention is not to limit the invention only to the specific embodiment shown but rather to include all modifications, alterations and equivalent arrangements possible within the scope of appended claims.

Figure 2:
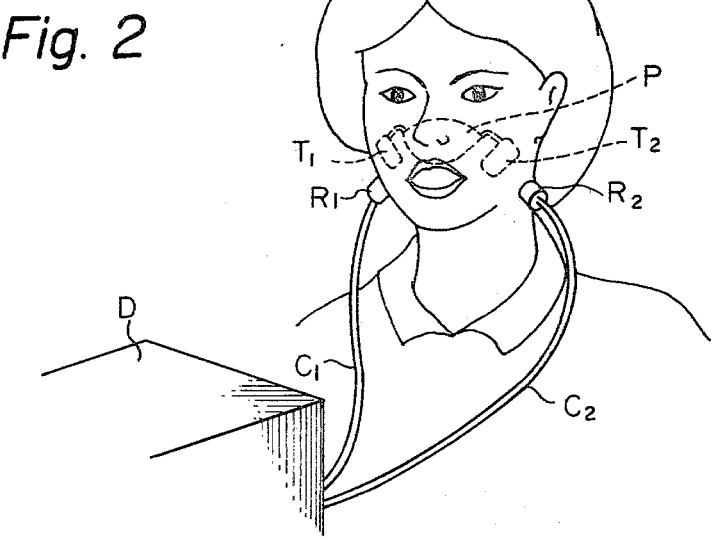
FIG. 2 is a view for explaining a similar state in which the training is performed but with a use of an electropalatograph according to a preferred embodiment of the present invention.

Referring to the preferred embodiment of the present invention with reference to FIG. 2, an artificial palate device P fitted in close contact with the hard palate surface within the mouth cavity of a trainee has a plurality of sensing electrodes with their sensing surface exposed on one surface of the device with which the trainee's tongue contacts, a plurality of lead wires respectively connected at one end to each of the sensing electrodes are divided into two right and left cords according to distributed positions of the electrodes and the cords are respectively led out of the device P and connected to each of a pair of tongue-contact signal transmitters $T_1$ and $T_2$ of the later described formation. The respective transmitters $T_1$ and $T_2$ are formed of small circuit elements so as to be of a very compact size as a whole and are positioned respectively between the right and left inner teeth and the cheeks with the respective cords passed behind the innermost ends of the upper tooth rows. On the other hand, a pair of receivers $R_1$ and $R_2$ receiving tongue-contact signals transmitted from the transmitters $T_1$ and $T_2$ are set by proper means preferably in positions adjacent the transmitters but outside the body of the trainee, the received signals are sent to a display device D through respective cords $C_1$ and $C_2$. The device D displays the detected linguapalatal contact mode in its dynamic pattern upon actual phonation or speech of the trainee in response to the tongue-contact signals.

Figure 1:
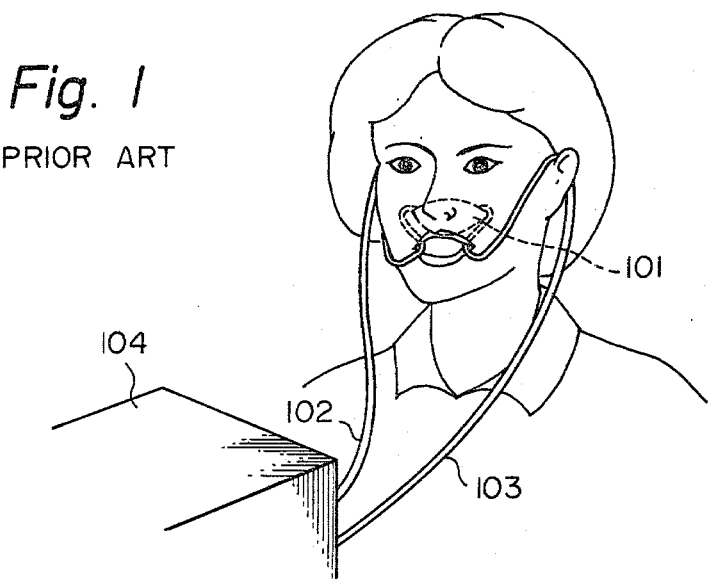
FIG. 1 is a view for explaining a state in which the articulation and speech training is performed using a conventional electropalatograph.
Figure 3:
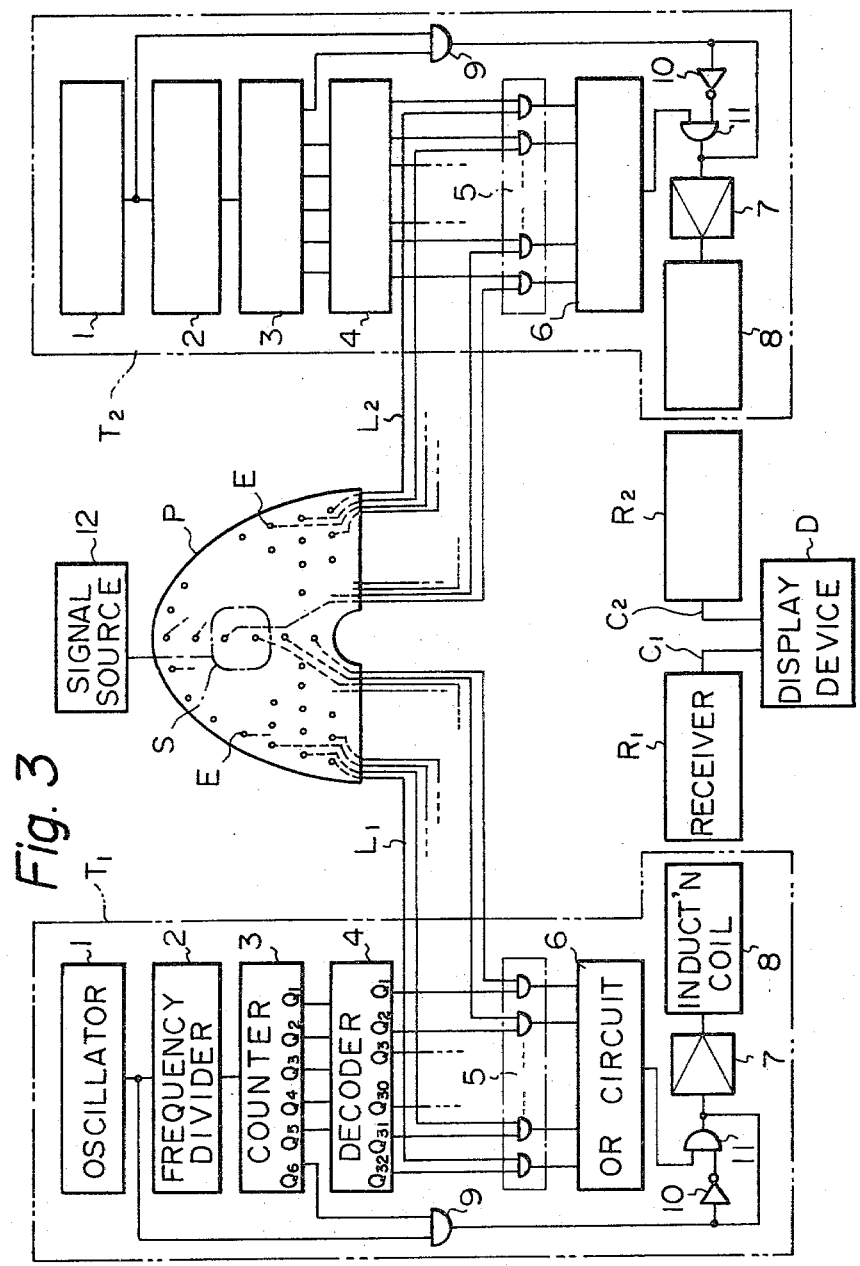
FIG. 3 is a block diagram showing an example of a practical circuit formation in particular of transmitters of the electropalatograph in the embodiment of FIG. 2.

A practical example of the formation of the transmitters $T_1$ and $T_2$ employed in this embodiment shall be described with reference to FIG. 3. In the present instance, the artificial palate device P has a signal electrode S connected with a signal source 12 and provided on the surface of the device to be brought into contact with the hard palate so that a predetermined signal voltage from the signal source 12 will be applied to the body of the trainee through the electrode S. On the opposite surface of the artificial palate device P with which the trainee's tongue contacts, in the present case, 64 of the sensing electrodes E are distributed as spaced substantially at regular intervals as explained with reference to FIG. 1, and each of right and left halves respectively of 32 pieces of these sensing electrodes E are connected to the respective tongue-contact signal transmitters $T_1$ and $T_2$ through two sets $L_1$ and $L_2$ of 32 lead wires. These transmitters $T_1$ and $T_2$ respectively have the same formation, wherein there is used, for example, an oscillator 1 generating pulses of such a comparatively high frequency as 20 KHz with a direct current source voltage from a very small current source battery preferably contained in each of the transmitters. The generated pulses are divided to be of 10 KHz in a frequency divider 2 and are sent to a 6-bit counter 3 which is provided with six output terminals $Q_1$ to $Q_6$ and divides the pulses of 10 KHz in the frequency respectively to be $\frac{1}{2}$ so that the counter 3 provides binary-coded signals of 64 digits to the output terminals $Q_1$ to $Q_6$. First five of the output terminals $Q_1$ to $Q_5$ are connected to five input terminals of a decoder 4 and this decoder receives from the output terminals $Q_1$ to $Q_5$ of the counter 3 sequentially 32 sets of the binary-coded signals corresponding to decimal digits from 0 to 31, repetitively. On the other hand, the decoder 4 is provided with 32 output terminals $Q_1$ to $Q_{32}$, so that 32 signals of H-level in the binary coded signals from the counter 3 will be caused to appear sequentially as a scanning signal at the respective output terminals $Q_1$ to $Q_{32}$ of the decoder 4. These 32 output terminals are respectively connected in turn to one of two input terminals of each of 32 AND gates of a gate circuit 5, and each of the lead wire bundles $L_1$ and $L_2$ of 32 lead wires from the artificial palate device P is connected to the other input terminal of the respective AND gates in accordance with the distributed positions of the sensing electrodes E on the artificial palate, so that a proper arranging order of these sensing electrodes will be set. Respective output terminals of these 32 AND gates of the gate circuit 5 are connected sequentially to each of 32 input terminals of an OR circuit 6, which has one output terminal connected to one of two input terminals of an AND gate 11. The output terminal of this AND gate 11 is connected through an amplifier 7 to a tongue contact signal transmitting means comprising, for example, an induction coil 8. On the other hand, the pulses generated in the oscillator 1 and binary coded signals provided to the sixth output terminal $Q_6$ of the counter 3 are respectively connected to a pair of input terminals of another AND gate 9, and the output terminal of this AND gate 9 is connected through an inverter 10 to the other input terminal of the AND gate 11 and also to a junction between the AND gate 11 and the amplifier 7.

For the respective components described above of the respective transmitters $T_1$ and $T_2$, the ones of micro sized type are employed and the transmitter as a whole is formed to be a small capsule made as flat as possible so as to be easily accommodated between the teeth and cheek.

The receivers $R_1$ and $R_2$ placed outside the trainee's body respectively comprise, in the present instance, an induction coil which receives the electromagnetic wave signals generated and transmitted by the induction coils 8 and converts them to corresponding electric signals, the thus converted signals are provided to the display device D through the cords $C_1$ and $C_2$ to be thereby treated so that, for example, 64 lamps arranged to coincide with the distributed positions of the sensing electrodes on the artificial palate P will be put on or off in response to the signals from the right and left receivers $R_1$ and $R_2$.

The operation of the transmitters $T_1$ and $T_2$ of the above described formation shall be explained in the following. In performing the articulation study or speech training as described above, the pulses of 20 KHz generated by the oscillator 1 are divided by the frequency divider 2 to be 10 KHz, the divided pulses are further divided to be $\frac{1}{2}$ by the 6-bit counter 3, and only the H-level signals from the output terminals $Q_1$ to $Q_5$ of the counter are provided as the scanning signal of 32 bits through the decoder 4 respectively sequentially to one of two input terminals of the respective 32 AND gates in the gate circuit 5. When the trainee to whom the predetermined signal voltage is being applied from the signal electrode S of the artificial palate P makes a phonation in this state, signals are provided from some of the sensing electrodes E on the artificial palate P which are contacted by the tongue at a mode of the particular phonation to the other input terminals of the AND gates in the circuit 5 which are corresponding to the sensing electrodes thus contacted, and these AND gates received the signals from these tongue-contacted electrodes are made open in a predetermined order at the time when they have received specific ones of the 32 scanning signals assigned to these AND gates, whereby the scanning signals to thus opened AND gates are passed to the OR circuit 6. Therefore, the OR circuit 6 sequentially receives at its 32 input terminals 32 H and L level signals and provides these signals in series to the single output terminal, and the AND gate 11 receives these series signals which are representing the linguapalatal contact mode of the particular phonation.

The AND gate 9 connected at the respective input terminals to the output side of the oscillator 1 and to the 6th output terminal $Q_6$ of the counter 3 is made open while the gate is receiving the first-half 32 sets of the binary-coded signals in the 64 set signals of 0 to 63 from the counter 3, but is closed while receiving the latter-half 32 sets from 32 to 63 of the binary-coded signals from the counter output terminal $Q_6$, so that the gate 9 will have the 20 KHz pulses from the oscillator 1 passed through the gate to the inverter 10 and amplifier 7. While the AND gate 9 is closed, that is, during the period of the binary coded signals from 0 to 31 from the counter 3, the output side of the inverter 10 is made to be at H-level so that the AND gate 11 will be open, whereby the series signals of the linguapalatal contact mode provided out of the OR circuit 6 will be fed to the amplifier 7 through the AND gate 11 and to the induction coil 8 to be thereby transmitted out of the transmitter $T_1$ or $T_2$ as the electromagnetic waves. On the other hand, during the period of the binary coded signals from 32 to 63 in which the AND gate 9 remains open, the output side of the inverter 10 will be at L-level in the same period and the 20 KHz pulses having passed through the AND gate 9 are sent directly to the amplifier 7 and transmitted in the form of the electromagnetic waves as converted by the induction coil 8. That is, the induction coil 8 in each of the right and left transmitters $T_1$ and $T_2$ sequentially transmits the tongue-contact mode informations with respect to the 32 sensing electrodes E on each of the right and left halves of the artificial palate P in the form of time series and then further transmits continuous signals of 20 KHz over the same period as that of the already transmitted informations as above. Therefore, these continuous signals of 20 KHz will act as a terminating signal of the tongue-contact mode informations on the 32 electrodes and, at the same time, as a starting signal of the next series of such informations. In this embodiment, as the linguapalatal contact mode pattern is displayed on the display device D by the same number of lamps in the same arrangement as those of the sensing electrodes, the display may be made in such that, for example, all of the lamps are normally kept lighted on by the continuous signals of 20 KHz and the lamps corresponding to the electrodes not contacted by the tongue are lighted off during the series tongue-contact mode informations.

While, in the above described embodiment, it is shown that the induction coil is employed as the tongue-contact signal transmitting means and the electromagnetic waves transmitted in response to the signals are received by the signal receiving means of the induction coil and converted to electric signals, the transmitting and receiving means may be of such other type than the induction coil as the one which generates and converts some other type of the electromagnetic wave such as a frequency-modulated (FM) or amplitude-modulated (AM) electric wave, light or the like. Further, in the right and left transmitters $T_1$ and $T_2$, at least the oscillator 1, the oscillator 1 and frequency divider 2 or the oscillator 1 through the counter 3 in the arrangement of FIG. 3 can be made only one or one set so as to be common to the right and left transmitters. The transmitter may be of course a single transmitter connected to all of the sensing electrodes without being divided into a pair of right and left transmitters. In order to produce the informations representing the tongue-contact modes in the time series signals, further, such means which can perform the same function as a shift register may be used instead of the same number of AND gates as the sensing electrodes. As regards the terminating or starting signal of the series tongue-contact informations, any other proper means may be employed in such that, for example, only one pulse of such scanning signals as has been described is made to be relatively large enough for rendering it distinguishable from other information signal pulses.

In the embodiment shown, further, there has been referred to a measure of detecting the linguapalatal contact mode by applying the signal voltage to the trainee's body through the single signal electrode S, providing such signal voltage through his tongue to the plurality of sensing electrodes E, and causing the AND gates in the gate circuit which are corresponding to the sensing electrodes contacted by the tongue to be opened. It is also possible to employ, however, a reverse measure of providing each of the scanning signals to all of the sensing electrodes E from the transmitters $T_1$ and $T_2$ by a proper means sequentially in accordance with the arranged positions of the electrodes, feeding the signals from the electrodes with which the tongue has contacted to the single electrode S through the tongue and hard palate of the trainee, transmitting as the electromagnetic waves the signals provided from the electrode S to a transmitter or transmitters disposed within the mouth cavity, and receiving the transmitted waves by the receivers $R_1$ and $R_2$ disposed outside the trainee's body. Further, instead of transmitting and receiving the tongue-contact signals in the series signal, the signals may be of course made to be parallel, but it will be appreciated that the particular transmitting and receiving arrangement referred to and shown is most preferable in view of the economy in the manufacturing cost.

As has been described above, according to the present invention, the means for transmitting and receiving the tongue-contact signals in a wireless type and set within the mouth cavity is used to display the linguapalatal contact modes in the dynamic patterns by electrically connecting the display device placed outside the body of the trainee with the artificial palate fitted within the mouth cavity, whereby the lead wire cords which have been conventionally required to be pulled out of the mouth cavity through the mouth lips of the trainee are not required, various problems caused by such cords are effectively eliminated, natural phonations and speeches can be easily performed, and the practical effect in the articulation study, speech training and the like with the electropalatograph of the kind referred to is remarkable.

What is claimed is:

1. An electropalatograph for speech training and the like comprising an artificial palate device to be mounted to a trainee's hard palate as adapted thereto and having on one surface contacted with the hard palate a single electrode, on the other surface with which the trainee's tongue contacts a plurality of tongue-contact sensing electrodes distributed substantially over the entire area of said the other surface as spaced from each other and a plurality of lead wires respectively connected at one end to each of said sensing electrodes, means connected to the other end of respective said lead wires to electrically detect contacting modes between said sensing electrodes and the tongue at the time of phonations for generating tongue-contact signals representing linguapalatal contact modes, and means for indicating said linguapalatal contact mode on the basis of said tongue-contact signals, said tongue-contact signal generating means including means for transmitting the tongue-contact signals as electromagnetic waves and being of a shape and dimensions capable of being accommodated within the trainee's mouth while allowing natural phonations to be performed, and said indicating means including means disposed outside the trainee's body for receiving said transmitted electromagnetic waves and converting received said waves into corresponding tongue-contact signals.

2. An electropalatograph according to claim 1 wherein said single electrode is connected to a signal voltage source disposed within the trainee's mouth, said tongue-contact signal generating means detects signal voltage provided through the trainee's tongue to said sensing electrodes to generate the tongue-contact signals.

3. An electropalatograph according to claim 2 wherein said tongue-contact signal generating means comprises means for sequentially scanning said plurality of sensing electrodes, and said scanning means selects the sensing electrodes to which said signal voltage is applied through the tongue and generates the tongue-contact signals.

4. An electropalatograph according to claim 2 wherein said tongue-contact signal generating means comprises a circuit which generates scanning signals for sequentially scanning said sensing electrodes, and a gate circuit opened by said scanning signals to pass said signal voltage provided from the sensing electrodes as the tongue contacts therewith to said transmitting means as the tongue-contact signals.

5. An electropalatograph according to claim 1 wherein said transmitting means comprises a pair of transmitters respectively connected through said lead wires to said sensing electrodes disposed in each of two halves of the entire area of said artificial palate device, and said receiving means comprises a pair of receivers respectively opposed to each of said pair of transmitters.

* * * * *